US005759856A

United States Patent [19]
Leder et al.

[11] Patent Number: 5,759,856
[45] Date of Patent: *Jun. 2, 1998

[54] CELL CULTURE SYSTEM

[75] Inventors: Philip Leder, Chestnut Hill, Mass.; Benjamin E. Rich, 85 Highland Rd., Brookline, Mass. 02146

[73] Assignee: Benjamin E. Rich, Boston, Mass.

[*] Notice: The term of this patent shall not extend beyond the expiration date of Pat. No. 5,459,058.

[21] Appl. No.: 477,071

[22] Filed: Jun. 7, 1995

Related U.S. Application Data

[62] Division of Ser. No. 342,643, Nov. 21, 1994, Pat. No. 5,459,058, which is a continuation of Ser. No. 119,315, Sep. 9, 1993, abandoned, which is a continuation of Ser. No. 939,976, Sep. 4, 1992, abandoned, which is a continuation of Ser. No. 676,816, Mar. 28, 1991, abandoned.

[51] Int. Cl.$^6$ .................................................. C12N 5/16
[52] U.S. Cl. ...................................... 435/373; 435/386
[58] Field of Search .......................... 435/240.2, 240.23, 435/240.4, 240.45, 240.46, 240.48, 373, 386

[56] References Cited

U.S. PATENT DOCUMENTS

| | | | |
|---|---|---|---|
| 4,914,032 | 4/1990 | Kuri-Harcuch et al. | 435/172.1 |
| 4,965,195 | 10/1990 | Namen et al. | 435/69.52 |
| 5,030,105 | 7/1991 | Kuri-Harcuch | 435/29 |
| 5,348,872 | 9/1994 | Lin et al. | 435/172.1 |
| 5,459,058 | 10/1995 | Leder et al. | 435/373 |
| 5,470,730 | 11/1995 | Greenberg et al. | 435/172.3 |

OTHER PUBLICATIONS

Whitlock et al., *J. Imm. Methods* 67:353, 1984.
Whitlock and Witte, *Meth. Enzymol.* 150:275, 1987.
Kincade et al., *Curr. Topics in Micro. & Imm.* 135:1, 1987.
Bentley, *Exp. Hematol.* 9:308, 1981.
Roberts et al., *J. Cell Physiol.* 132:203, 1987.
Dennis and Witte, *Proc. Natl. Acad. Sci. USA* 83:441, 1986.
Dorshkind, *J. Immunol.* 136:422, 1986.
Witte et al., *Eur. J. Immunol.* 17:1473, 1987.
Kierney and Dorshkind, *Blood* 70:1418, 1987.
Pietrangeli et al., *Eur. J. Immunol.* 18:863, 1988.
Piersma et al., *Exp. Hematol.* 13:237, 1985.
Hunt et al., *Cell* 48:997, 1987.
Ogawa et al., *EMBO J.* 7:1337, 1988.
Williams et al., *Mol. Cell Biol.* 8:3864, 1988.
Landreth and Dorshkind, *J. Immunol.* 140:845, 1988.
Lemoine et al., *Cancer Res.* 48:6438, 1988.
Kincade, *Adv. in Immunol.* 41:181, 1987.
Dorshkind, *Ann. Rev. Immunol.* 8:111, 1990.
Kincade et al., *Ann. Rev. Immunol.* 7:111, 1989.
Namen et al., *J. Exp. Med.* 167:988, 1988.
Namen et al., *Nature* 333:571, 1988.
Goodwin et al., *Proc. Natl. Acad. Sci USA* 86:302, 1989.
Takeda et al., *Proc. Natl. Acad. Sci. USA* 86:1634, 1989.
Hayashi et al., *J. Exp. Med.* 171:1683, 1990.
Welch et al., *J. Immunol.* 143:3562, 1989.
Chazen et al., *Proc. Natl. Acad. Sci USA* 86:5923, 1989.
Grabstein et al., *J. Immunol.* 144:3015, 1990.
Williams et al., *Blood* 75:1132, 1990.
Morrissey et al., *J. Exp. Med.* 169:707, 1989.
Gunning et al., *Proc. Natl. Acad. Sci USA* 84:4831, 1987.
Borzillo et al., *Mol. Cell Biol.* 10:2703, 1990.
Rettenmier et al., *Mol. Cell. Biol.* 7:2378.
Lander, *Mol. Neurobiol.* 1:213, 1987.
Bienenstock et al., *Int. Archs Allergy Appl. Immun.* 82:238, 1987.
Azmitia et al., *Neurobiol. of Aging* 9:743, 1988.
Carbonetto and Cochard, *J. Physiol., Paris* 82:258, 1987.
Chiquet and Nicholls, *J. Exp. Biol.* 132:191, 1987.
Bunge et al., *Brain Res.* 78:321, 1988.
McMahon and Bradley, *Cell* 62:1073, 1990.
Folkman and Klagsbrun, *Science* 235:422, 1987.
Ingber and Folkman, *J. Cell Biol.* 109:317, 1989.
Ingber et al., *In Vitro Cell. & Dev. Biol.* 23:387.
Audus et al., *Pharm. Res.* 7:435, 1990.

*Primary Examiner*—James Ketter
*Attorney, Agent, or Firm*—Fish & Richardson P.C.

[57] ABSTRACT

Disclosed is a method for the culture of higher eukaryotic cells which are dependent for survival on an exogenous factor. The method involves co-culturing the factor-dependent cells with an immortalized eukaryotic cell that has been engineered to secrete the requisite factor.

Also disclosed is a cell line of non-stromal cell origin which secretes interleukin-7.

20 Claims, 3 Drawing Sheets

CELL CULTURE SYSTEM

This is a divisional of application Ser. No. 08/342,643, filed Nov. 21, 1994, now U.S. Pat. No. 5,459,058 which is a continuation of application Ser. No. 08/119,315, filed Sep. 9, 1993, now abandoned, which is a continuation of application Ser. No. 07/939,976, filed Sep. 4, 1992, now abandoned, which is a continuation of application Ser. No. 07/676,816, filed Mar. 28, 1991, now abandoned.

BACKGROUND OF THE INVENTION

This invention relates to in vitro cell culture systems.

Given the appropriate conditions, many types of mammalian cells may be propagated in vitro. Typically, such conditions include a chemically-defined growth medium containing essential amino acids (e.g., cysteine, glutamine, and tyrosine), vitamins (e.g., biotin, choline, folic acid, thiamine), salts (e.g., NaCl, KCl, $CaCl_2$), glucose, and, in many cases, serum. The role of serum is not completely understood, however it is purported to provide requisite trace materials, e.g., protein growth factors. In addition to a defined culture medium, many cultured mammalian cells require a solid surface on which to grow and divide. This requirement is most often provided by a glass or plastic tissue-culture dish or flask. In the absence of such a requirement, cells may be grown in suspension, e.g., in a test tube or tissue-culture bottle.

Two types of cultured mammalian cells are in widespread experimental and industrial use: "primary cells" and "immortalized cells". Primary cells are prepared directly from the normal tissues of an organism, e.g., from skin, bone marrow, or whole embryos. These cells grow well when first placed under culture conditions, typically surviving for weeks or months and dividing for about 50–100 generations. At that time, cells reach a stage, termed "crisis"; they grow and divide slowly, and soon, thereafter, cease to grow and divide altogether.

Immortalized cells are characterized by indefinite growth in vitro. Typically, immortalized cell cultures are derived either from a tumor sample explanted directly from an organism or from a primary cell variant which has undergone a change which promotes indefinite growth.

Hematopoietic cells may be propagated as primary cell cultures in vitro. Growth factors are provided, either by exogenous addition of the factors to the culture medium or by secretion of the factors by "feeder cells". Such feeder cells are generally stromal cells (i.e., a poorly defined mix of primary cells derived from bone marrow). A description of hematopoietic cell culture involving a stromal cell feeder layer is described by Whitlock et al. (*J. Imm. Methods* 67:353, 1984) and Whitlock and Witte (*Meth. Enzymol* 150:275, 1987); using their method, continuous cultures of early B-lymphocytes are established on an adherent feeder layer of dissociated mouse bone marrow cells. There is some support for the idea that hematopoietic cell growth also requires cell-cell contact. For example, Kincade et al. (*Curr. Topics in Micro. & Imm.* 135:1, 1987) report the dependence of cultured lymphoid cells on substances produced by, and/or on physical association with, an adherent stromal cell layer.

SUMMARY OF THE INVENTION

In general, the invention features a method for culturing a higher eukaryotic cell which is dependent for survival upon an exogenous factor. The method involves co-culturing the factor-dependent cell with an immortalized higher eukaryotic cell that has been engineered to secrete the requisite exogenous factor.

In preferred embodiments, the cell dependent for survival upon an exogenous factor is further dependent for survival on cell-cell contact; is a non-adherent cell; is a mammalian cell, preferably, a human cell; and is a ematopoietic cell, preferably, a B-lineage lymphocyte, a T-lineage lymphocyte, or a thymocyte; the immortalized higher eukaryotic cell is an adherent cell; is a mammalian cell, preferably, a human cell; and is a fibroblast cell, preferably, an NIH3T3 cell; the exogenous factor is interleukin-7; the interleukin-7 is expressed from a stably transfected gene in the immortalized higher eukaryotic cell; the stably transfected gene includes an enhancer; the interleukin-7 is encoded by plasmid pBAIL-7; and the culturing is long-term.

In another preferred embodiment, the method further involves contacting the immortalized higher eukaryotic cell with a growth-inhibitory amount of mitomycin-C just prior to co-culturing with the higher eukaryotic cell which is dependent for survival upon an exogenous factor.

In a related aspect, the invention features a cell line of non-stromal cell origin that secretes interleukin-7. In preferred embodiments, the cell line harbors a transgene that directs expression of interleukin-7; the transgene comprises an enhancer, preferably, an actin enhancer; the cell line is a mammalian cell line, preferably, a fibroblast cell line, more preferably, an NIH3T3 cell line, and, most preferably, NAIL-7.

By "higher eukaryotic cell" is meant a cell which contains a nucleus and is derived from a multicellular organism. The term, as used herein, does not include a yeast cell. By "dependent for survival upon" is meant to require for survival and/or growth or proliferation. By "immortalized" is meant able to grow (i.e., produce progeny cells) indefinitely in cell culture. By "non-stromal cell origin" is meant not deriving from a bone marrow explant. By "secrete" is meant to export a substance, e.g., a factor from the inside to the outside of a cell. The term includes export by either active or passive mechanisms. By "factor" is meant any substance which a cell requires to survive and/or grow and/or proliferate and which can be produced and exported by another cell. Such factors include, without limitation, growth factors (e.g., interleukins, insulin, transferrin, hydrocortisone, fibroblast growth factor, nerve growth factor, epidermal growth factor), amino acids, and vitamins. By "cell-cell contact" is meant a physical association between two cells. By "adherent" is meant capable of maintaining contact with a solid support for a substantial period of time; the solid support is, preferably, a cell culture dish or flask and the substantial period of time is, preferably, all or most of the generation time of the cultured cell. By "stably transfected gene" is meant a piece of DNA encoding a protein which is inserted by artifice into a cell and becomes heritably transmitted to progeny cells. Such a stably transfected gene may be partly or entirely heterologous to the host cell and may be inserted into the host cell genome at the same or at a different location (e.g., a modified gene which is homologously recombined into the host genome replacing the endogenous genomic sequence); alternatively, such a stably transfected gene may be a gene homologous to a natural gene of the host cell, but which is inserted into the host cell's genome at a location which differs from that of the natural gene. By an "enhancer" is meant a cis-acting DNA sequence capable of increasing transcription from a promoter that is located either upstream or downstream of the enhancer region. Such enhancer DNA sequences are well known to those skilled in the art of eukaryotic gene expression. By "B-lineage lymphocytes" is meant a hematopoietic cell which matures into an immunoglobin-producing cell. By "thymocyte" is meant a cell which resides during part of its in vivo existence in the thymus and which is a precursor to a "T-lineage lymphocyte". By "hematopoietic cell" is meant a blood cell whether developmentally mature or immature, or a precursor of a blood cell. By "long-term" culture is meant culture which extends for a continuous period of time which is generally greater than one month.

This invention is based on the discovery that NIH 3T3 cells (i.e., immortalized, higher eukaryotic cells) that have been engineered to produce IL-7 can support the long-term growth and proliferation of factor-dependent hematopoietic cells, in particular, B-lineage lymphocytes. Such feeder layers stimulate rapid B-lineage lymphocyte proliferation and permit a high final B-lymphocyte cell density.

The invention provides a convenient alternative to the culture of factor-dependent cells on primary feeder layers. For example, the methods of the invention do not require the sacrifice of animals (e.g., mice) nor do they involve an extended period of time for establishment of a feeder layer (e.g., 2–4 weeks for establishment of a stromal cell feeder layer). In addition, the feeder layers of the invention are composed of a clonal population of cells. This facilitates a predictable and reproducible method of cell culture through the provision of defined growth conditions. Use of a clonal feeder layer also circumvents problems of "contamination" by undesirable cells (e.g., those present in a stromal cell population) which grow very rapidly and compete with the factor-dependent cells for nutrient sources and/or cell-cell contact. In the worst case, contaminating cells may actually destroy the factor-dependent cells through secretion of toxins or by phagocytosis.

Other features and advantages of the invention will be apparent from the description of the preferred embodiments, and from the claims.

DETAILED DESCRIPTION OF DRAWINGS

The drawings will first briefly be described.

Figure 1:
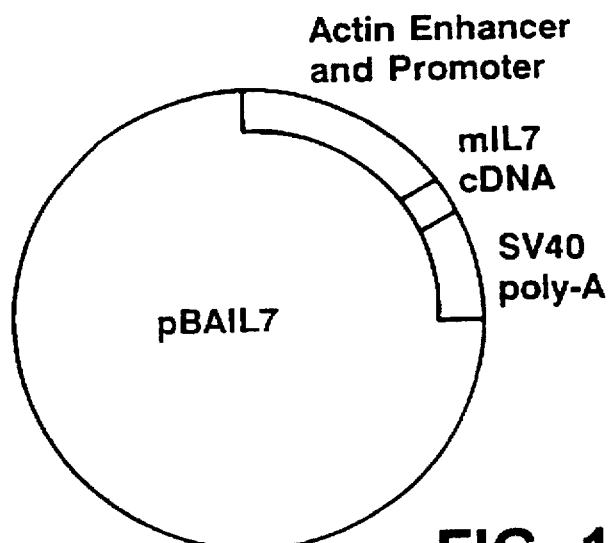
FIG. 1 is a diagram of the IL-7 expression vector, pBAIL7.

There now follows one example of an immortalized mammalian cell line (i.e., the NAIL-7 cell line) which has been engineered to produce and secrete a factor (i.e., IL-7) and a description of its use as a feeder layer for the culture of hematopoietic cells (i.e., B-lineage cells) which are dependent for their survival upon both the factor and cell-cell contact. This example is presented for the purpose of illustrating, not limiting, the invention.

The NAIL-7 Cell Line.

The pBAIL-7 expression plasmid and the NAIL-7 cell line were constructed as follows.

A cDNA library was first prepared. mRNA was extracted from the spleen of a Swiss mouse by the guanidinium isothiocyanate method of Chirgwin (*Biochemistry* 18:5294, 1976), and cDNA produced from this RNA using the cDNA synthesis kit of Boehringer-Mannheim (Indianapolis, IND.) and the recommendations of the manufacturer. Oligodeoxynucleotide PCR primers were designed based on the published IL-7 sequence of Namen et al. (*Nature* 333:571, 1988) and generated by an Applied Biosystems 380A DNA Synthesizer (Applied Biosystems, Foster City, Calif.). The sequences of the primers corresponded to nucleotides 525–551 of the IL-7 positive sense strand and 1158–1184 of the IL-7 negative sense strand. In addition, four nucleotides, GGTC, were included at the 5' end of each primer to create a SalI restriction enzyme recognition site in the PCR product. $0.1 \times 10^9$ moles of each PCR primer were mixed with 4µg of spleen cDNA, and an IL-7 cDNA molecule was amplified by the polymerase chain reaction (PCR) procedure of the Cetus Corporation (Perkin-Elmer Cetus Gene Amp Kit, Norwalk, Conn.). PCR-amplified reaction products were treated with polynucleotide kinase to add 5' terminal phosphate groups and the fragments were ligated to SmaI-digested, pBluescript KS (Stratagene, La Jolla, Calif.). *E. coli* strain DH5α was transformed with the ligation mixture and ampicillin-resistant cells (i.e., those cells harboring a recombinant plasmid) were selected and propagated in culture by standard techniques (see, e.g., Ausubel et al., *Current Protocols in Molecular Biology*, Wiley Publishing, New York, N.Y., 1987). Plasmid DNA was prepared by standard techniques (Ausubel et al., *supra*), and the sequences of the cDNA inserts were determined by the method of Sanger (Sanger et al., *Proc. Natl. Acad. Sci. USA* 74:5463, 1977). Clone pIL-7.16 was shown to contain a full-length IL-7 coding sequence and was used for all subsequent subcloning procedures.

To direct expression of IL-7 in NIH3T3 cells, the IL-7 cDNA was inserted downstream of (i.e. under the transcriptional control of) the human β-actin enhancer and promoter, transcriptional control elements which have been shown to be highly active in NIH3T3 cells (Gunning et al., *Proc. Natl. Acad. Sci. USA* 84:4831, 1987). The expression plasmid was constructed as follows. pIL7.16 was digested with SalI and a 668 base pair fragment containing the IL-7 CDNA was isolated by agarose gel electrophoresis (Ausubel et al., *supra*). This fragment was ligated to SalI-digested pHBApr-1 (Gunning et al., *Proc. Natl. Acad. Sci. USA* 84:4831, 1987) and used to transform *E. coli* DH5βhost cells as described above. Plasmid DNA was prepared from several independent colonies and was screened by restriction digestion analysis using the published IL-7 and pHBApr-1 sequences described above. A recombinant plasmid with the IL-7 cDNA in the appropriate orientation was selected and termed pBAIL-7 (β-Actin/IL-7).

pBAIL-7 was introduced into cultured mammalian NIH3T3 cells as follows. 20 µg of ScaI-digested pBAIL-7 and 1 µg of EcoRI-digested pSV7neo (Murphy et al., *Proc. Natl. Acad. Sci. USA* 83:2939, 1986) were mixed with $10^7$ NIH3T3 fibroblasts (ATCC Accession Number CRL-6442) in 0.5 ml of phosphate buffered saline. pSV7neo confers resistance to G418, and cells transfected with this plasmid may be dominantly selected (Ausubel et al., *supra*). Cells were electroporated by standard techniques using a BioRad Gene Pulser machine (0.25 Kv, 960 uF) (BioRad, Hercules, Calif.; Ausubel et al., *supra*), incubated for two days in nonselective medium (i.e., Dulbecco's Modified Eagle Medium, or DMEM, supplemented with 2 mM glutamine, 50 U/ml penicillin, 50 µg/ml streptomycin, and 10% bovine calf serum; GIBCO, Grand Island, N.Y.), and then incubated for 11 days in selective medium (i.e., DMEM containing 400 µg/ml G418; Geneticin; Life Technologies Inc., Grand Island, N.Y.). Twelve G418-resistant clones were selected and transferred to individual plates with a capillary tube. Clones were propagated for several generations in selective medium, aliquots of cells were then propagated in nonselective medium, and their culture supernatants were assayed for the production of IL-7 by the method of Namen et al. (*J. Exp Med.* 164:988–1002, 1988). In addition, RNA was prepared from samples of the clones by the method of Chirgwin (*Biochemistry* 18:5294, 1976) and assayed for the presence of IL-7 MRNA by RNase protection (by the method of Krieg et al., Nucl. Acids Res. 12:7035–56, 1984) using an IL-7-specific probe including nucleotides 525 to 656 of the anti-sense strand of pIL7.16. One cell line shown to express IL-7 MRNA and secrete active IL-7 was chosen for experiments described herein. This cell line was termed NAIL-7 (NIH3T3/β-Actin/IL-7).

Lymphocyte Cultures

A monolayer of NAIL-7 cells was used to support the growth of B-lineage lymphocytes and the efficacy of such a NAIL-7 feeder layer was compared to that of a parental NIH3T3 cell layer and a primary stromal cell layer.

Primary stromal cell feeder layers were prepared by the method of Whitlock et al. (*J. Imm. Meth.* 67:353–369, 1984). NAIL-7 and NIH3T3 cell feeder layers were prepared by treating confluent cultures of each cell type with mitomycin-C (10 µg/ml for 2–4 hr., Sigma Chemical Co., St. Louis, Mo.) to block cell division. Following treatment, cells were replated at $5 \times 10^4$ cells/cm$^2$.

Feeder-dependent B-lineage lymphocytes were prepared from BALB/c mice by the method of Whitlock et al., (*J. Imm. Meth.* 67:353, 1984) and were plated at $10^5$ cells/ml in dishes containing monolayers of either stromal cells, mitomycin-C-treated NIH3T3 cells, or mitomycin-C-treated NAIL-7 cells (each prepared as described above). At 3–4 day intervals, the cultures were alternately supplemented with a half-volume of selective medium, or resuspended vigorously, aspirated, and replenished with one volume of selective medium. The cells in the aspirates were counted by standard techniques.

Figure 2:
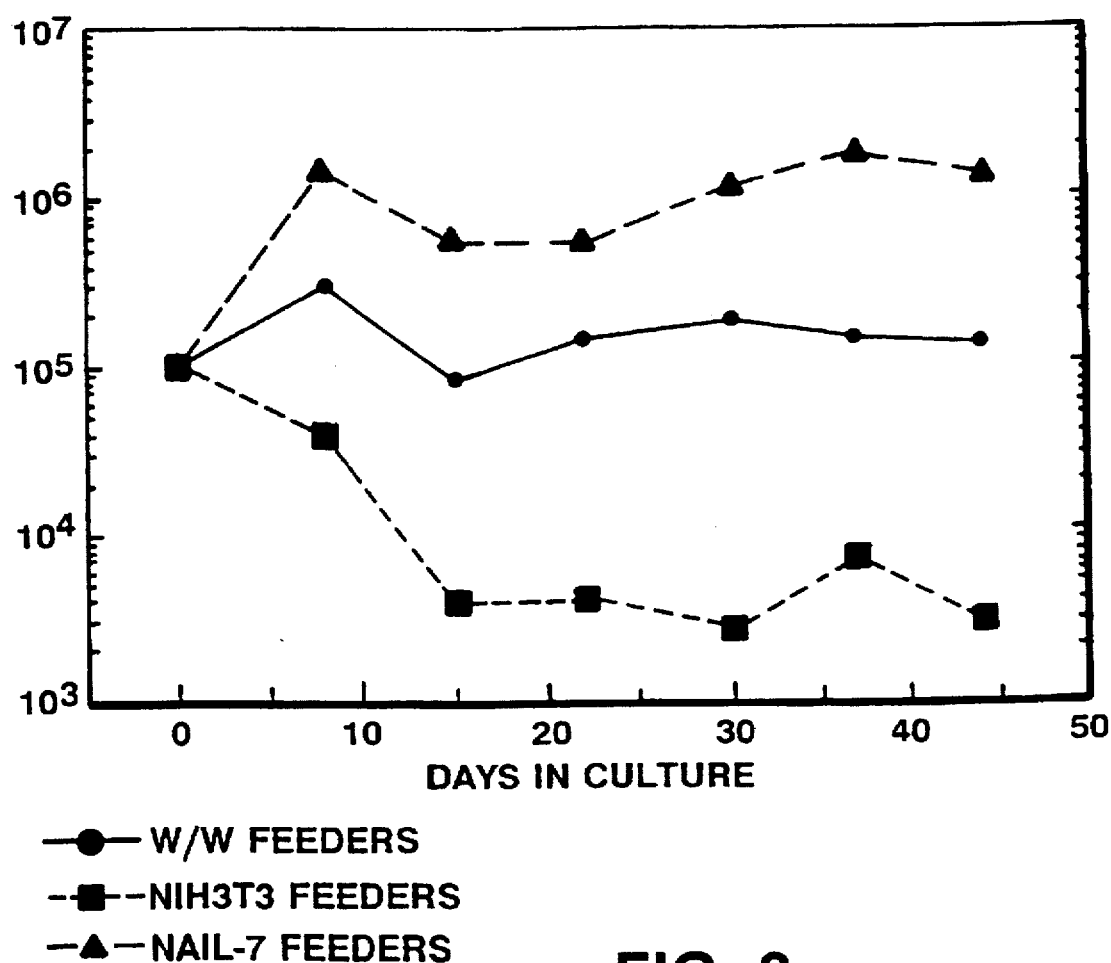
FIG. 2 is a graph showing lymphocyte proliferation on three different adherent mammalian cell lines.
Figure 3A:
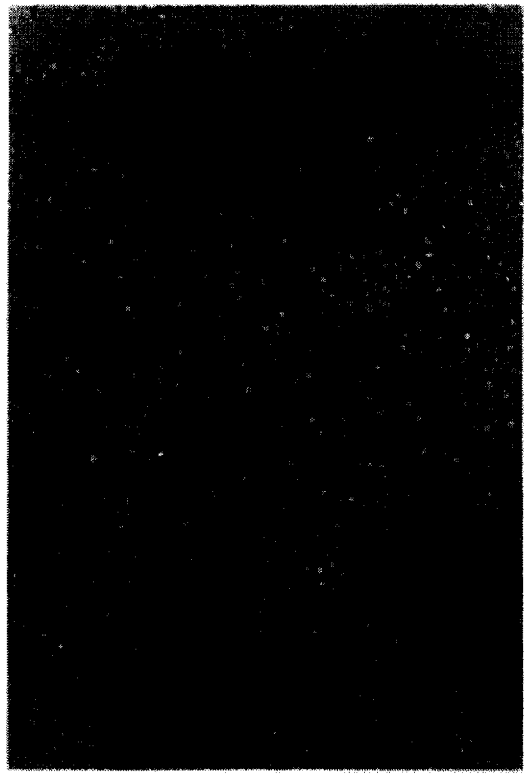
FIG. 3 is a representation of a series of micrographs showing B-lymphocytes cultured on an adherent layer of (A) primary bone marrow-derived feeder cells, (B) NAIL-7 feeder cells, and (C) NIH 3T3 feeder cells.
Figure 3B:
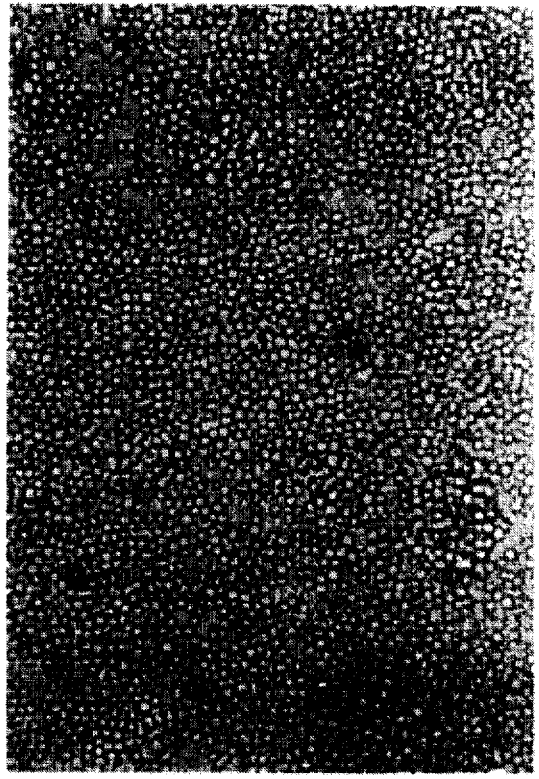
Figure 3C:
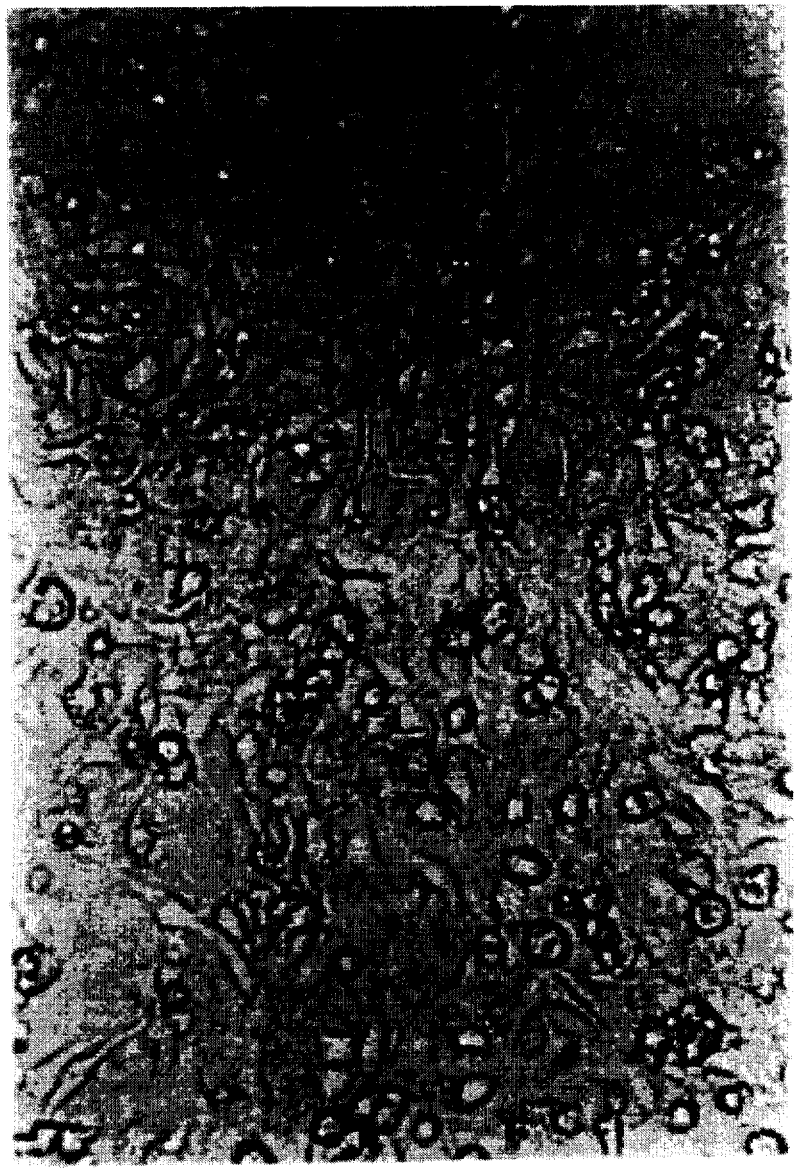

Results presented in FIG. 2 show the number of B-lymphocytes in cultures grown on either NAIL-7 cells (▲), NIH3T3 cells (■), or bone marrow stromal cells (●). FIG. 3 shows feeder-dependent lymphocytes grown for 10 days on either NAIL-7 cells (middle panel, B) or NIH3T3 cells (right panel, C). FIG. 3 also shows a six week culture of bone marrow stromal cells (left panel, A). FIGS. 2 and 3 indicate that feeder-dependent lymphocytes cultured on primary bone marrow stromal cells or on NAIL-7 cells proliferated vigorously while the same lymphocytes plated on NIH3T3 cells grew very poorly, if at all. FIG. 2 further shows that B-lymphocytes grow rapidly and to a higher density on NAIL-7 cells than on a stromal cell feeder layer or on an NIH3T3 cell layer.

Certain aspects of this method may be altered without destroying the efficacy of the culture system. For example, although it is preferable to routinely transfer aliquots of the cultured B-lymphocytes to plates containing freshly mitomycin C-treated NAIL-7 cell layers (e.g., once a week to once a month), a continuous culture of B-lymphocytes may be successfully propagated on a single layer of treated NAIL-7 cells for many months. To date, B-lymphocytes have been cultured for up to eight continuous months on the same layer of mitomycin-C treated NAIL-7 cells.

B-lymphocytes have also been propagated on a NAIL-7 cell line which was not treated with mitomycin-C. Culture was carried out as described above (i.e., using equivalent medium lacking mitomycin-C) except that the NAIL-7 feeder layer was plated at a very low initial density (e.g., at 1/10 confluence or approximately $10^4$ cells or less/10 cm$^2$ plate). The length of continuous culture time is limited by the rapid growth of the untreated NIH3T3 feeder layer and the resultant exhaustion of culture nutrients.

Examples of Other Culture Systems

The method of the invention can be used to culture factor-dependent cells remote from B-lineage lymphocytes and can utilize feeder cell layers other than IL-7-producing NIH3T3 cells. The following examples illustrate that such feeder cells and such factor-dependent cells may be either adherent or non-adherent. These examples are designed to provide guidance and should not be construed as limiting.

Culture of adherent factor-deDendent cells with non-adherent feeder cells

In a first example, adherent factor-dependent cells are propagated with non-adherent feeder cells The factor-dependent cells are plated on a solid support, e.g., on a tissue culture dish, under conditions and for a period of time which allow adherence to the solid support. Feeder cells are then suspended in the culture medium, where they secrete factors which promote adherent cell growth. Harvesting the factor-dependent cells involves removal of the feeder cells by aspiration of the culture supernatant followed, where necessary, by one or more washing steps with, e.g., phosphate buffered saline. The factor-dependent cells are then collected following their release from the solid support, e.g., by brief treatment with trypsin (by standard methods; see, e.g., Ausubel et al., *supra*).

In particular, this method of this first example may be used for the propagation of adherent factor-dependent endothelial cells with engineered non-adherent hematopoietic cells, e.g., lymphocytes. The endothelial cells and hematopoietic cells are cultured by standard techniques (see, e.g., Andus et al., *Pharm. Res.* 7:435, 1990; and methods described herein, respectively). The hematopoietic cells are engineered to produce a factor which stimulates endothelial cell growth, such as fibroblast growth factor, transforming growth factor-α, transforming growth factor-β, or the c-kit ligand (see, e.g., Folkman et al., *Science* 235:442, 1987; Ingber et al., *J. Cell Biol.* 109:317, 1989). Following propagation, the endothelial cells are harvested as decribed above.

Culture of adherent factor-dependent cells with adherent feeder cells

In a second example, both the factor-dependent cells and the feeder cells are adherent. In this case, cells are plated simultaneously and allowed to adhere to a solid support (preferably, a tissue culture dish, as generally described above). The factor-dependent cells are stimulated to divide by growth factors produced by the adherent feeder cells. Following propagation, the factor-dependent cells and the feeder cells are simultaneously harvested by brief treatment with trypsin (as described above). Factor-dependent cells are isolated from the mixed population by physical methods designed to differentiate between the two cell types, e.g., elutriation or density gradient centrifugation (Beckman Publications DS 534; Beckman Instruments, Columbia, Md.; Ausubel et al., *supra*; respectively). The factor-dependent cells may also be isolated by immunological methods, such as binding to cell type-specific monoclonal antibodies attached to plastic plates or magnetic beads (Wysocki and Sato, *Proc. Natl. Acad. Sci. USA* 75:2844, 1978; Dynal, Inc. Great Neck, N.Y.), or to fluorescent molecules for fluorescence activated cell sorting (Jovin et al., *Trends Biochem. Sci.* 5:214, 1980; Herzenberg et al., *Sci. Am.* 234:108, 1976; Ortho Diagnostics Systems, Inc., Westwood, Mass.).

In specific examples, this method is useful for the culture of factor-dependent endothelial cells or factor-dependent nerve cells on an engineered NIH3T3 feeder layer. In the first case, the feeder layer cells are engineered to produce endothelial cell growth factors such as fibroblast growth factor, transforming growth factor-α, transforming growth factor-β, or kit ligand (see, e.g., Folkman et al., 1987, *supra*; Ingber et al., 1989, *supra*). In the second case, the immortalized adherent cells are engineered to produce a nerve cell growth factor such as nerve growth factor (NGF) (see, e.g., Bienenstock et al., *Int. Arch. Allergy Appl. Immunol.* 87:238, 1987; Carbonetto et al., *J. Physiol.* (Paris) 82:258, 1987). Cells are grown using standard methods of endothelial cell or nerve cell culture (see, e.g., Audus et al., *Pharm. Res.* 7:435, 1990; and Lander, Mol. *Neurobiol.* 1:213, 1987; Bunge et al., Prog. *Brain Res.* 78:321, 1988; Azmitia et al., *Neurobiol of Aging* 9:743, 1988, respectively). The factor-dependent cells are separated by physical or immunological methods as described above.

Culture of non-adherent factor-dependent cells with nonadherent feeder cells

Finally, both the factor-dependent cells and the feeder cells may be non-adherent. In this case, factor-dependent cells and feeder cells are cultured as a mixed population in solution (e.g., in a test tube or culture bottle). Once propagated, the factor-dependent cells are harvested by physical or immunological separation from the feeder cells, using, for example, the methods described above. Alternatively, factor-dependent cells not requiring cell-cell contact may be grown in solution with feeder cells, under conditions where the factor-dependent cells remain separated from the feeder cells by some physical barrier, e.g., a semi-permeable membrane. Such a physical barrier must prevent cells from mixing but must allow factor(s) to pass from the feeder cells to the factor-dependent cells. Preferably, the physical barrier used for this type of culturing is provided by a Millicell-CM (Millipore, Bedford, Mass.).

In a specific example, this method is used for the culture of factor-dependent B-lymphocytes with engineered T-lymphocyte feeder cells. Cells are grown using standard methods of lymphocyte cell culture (see, e.g., methods described herein). The feeder cells are engineered to produce a B-lymphocyte growth factor, such as IL-7 (as described herein). If the factor-dependent and feeder cells are cultured together in suspension, the factor-dependent cells are separated by physical or immunological methods as described above. Alternatively, if the factor-dependent cells and feeder cells are cultured on opposite sides of a semi-permeable membrane, the need for later separation is circumvented, and the factor-dependent cells may be harvested directly from suspension.

For all of the above examples, the choice of culture conditions (e.g., choice of growth medium) will vary slightly according to the types of feeder and factor-dependent cells involved; appropriate conditions are well known by those skilled in the art. Where necessary, culture conditions are adjusted to accommodate the growth condition requirements (e.g., media requirements) of both the feeder cells and the factor-dependent cells, the modifications are generally minor and should not be an impediment to the success of the culture method.

Other Embodiments

Mitomycin-C treatment is not necessary to the success of the instant culture method. Mitomycin-C treatment facilitates the use of feeder layers capable of rapid proliferation; however, as described above, untreated feeder layers have been used successfully (even very rapidly-dividing NIH3T3 feeder layers). Moreover, since mitomycin-C treatment simply slows feeder layer proliferation, it may be eliminated when the culture system makes use of a slowly-dividing feeder layer.

The method of the invention may be used for the propagation of human cells, for example, B- or T-lineage lymphocytes. Because the culture system provides the opportunity to define the growth conditions, particular growth factors may be provided by the feeder layer which stimulate maturation of, e.g., blood cells from progenitor cells. Alternatively, omission of a growth factor which triggers cell differentiation (e.g., one which is normally secreted by primary cell layers, such as stromal cells) allows the large-scale propagation of cell precursors, e.g., stem cells. In one particularly useful application, human cells are isolated from a patient, e.g., stem cells or blood cells from an immunodeficient or immunocompromised patient. The cells are propagated using the in vitro method of the instant invention, harvested, and re-introduced (e.g., intravenously) into the patient to bolster or restore immune function.

We claim:

1. A method for culturing an animal cell which is dependent for survival upon an exogenous factor, said method comprising co-culturing said cell with an immortalized animal cell that expresses and secretes said factor.

2. The method of claim 1, wherein said cell dependent for survival upon an exogenous factor is further dependent for survival on cell-cell contact.

3. The method of claim 1, wherein said cell dependent for survival upon an exogenous factor is a non-adherent cell.

4. The method of claim 1, wherein said cell dependent for survival upon an exogenous factor is a mammalian cell.

5. The method of claim 4, wherein said mammalian cell is a human cell.

6. The method of claim 1, wherein said cell dependent for survival upon an exogenous factor is a hematopoietic cell.

7. The method of claim 6, wherein said hematopoietic cell is a B-lineage lymphocyte.

8. The method of claim 6, wherein said hematopoietic cell is a T-lineage lymphocyte.

9. The method of claim 6, wherein said hematopoietic cell is a thymocyte.

10. The method of claim 1, wherein said immortalized animal cell is an adherent cell.

11. The method of claim 1, wherein said immortalized animal cell is a mammalian cell.

12. The method of claim 11, wherein said mammalian cell is a human cell.

13. The method of claim 1, wherein said immortalized animal cell is a fibroblast cell.

14. The method of claim 13, wherein said fibroblast cell is an NIH3T3 cell

15. The method of claim 1, wherein said culturing is long-term.

16. The method of claim 1, further comprising contacting said immortalized animal cell with a growth-inhibitory amount of mitomycin-C just prior to co-culturing with said animal cell which is dependent for survival upon an exogenous factor.

17. The method of claim 1, wherein said cell dependent for survival upon an exogenous factor is a lymphoid cell.

18. A method for culturing a lymphoid cell which is dependent for survival upon an interleukin, said method comprising co-culturing said cell with an immortalized animal cell that expresses and secretes said interleukin.

19. The method of claim 18, wherein said cell dependent for survival upon an exogenous factor is a hematopoietic cell.

20. The method of claim 18, wherein said cell dependent for survival upon an exogenous factor is a lymphoid cell.

* * * * *